United States Patent [19]
Suzuki et al.

[11] Patent Number: 5,103,829
[45] Date of Patent: Apr. 14, 1992

[54] EXAMINATION APPARATUS FOR MEASURING OXYGENATION IN BODY ORGANS

[75] Inventors: Susumu Suzuki; Sumio Yagi; Naotoshi Hakamata; Takeo Ozaki, all of Shizuoka, Japan

[73] Assignee: Hamamatsu Photonics Kabushiki Kaisha, Shizuoka, Japan

[21] Appl. No.: 189,257

[22] Filed: May 2, 1988

[30] Foreign Application Priority Data

| May 8, 1987 | [JP] | Japan | 62-67858[U] |
| May 8, 1987 | [JP] | Japan | 62-110461 |
| May 8, 1987 | [JP] | Japan | 62-110466 |
| May 8, 1987 | [JP] | Japan | 62-110471 |

[51] Int. Cl.$^5$ ............................................. A61B 5/14
[52] U.S. Cl. ..................................................... 128/633
[58] Field of Search ................ 128/633, 634, 664, 665

[56] References Cited

U.S. PATENT DOCUMENTS

| 4,223,680 | 9/1980 | Jobsis | 128/633 |
| 4,281,645 | 4/1983 | Jobsis | 128/633 |
| 4,321,930 | 3/1982 | Jobsis et al. | 128/633 |
| 4,380,240 | 4/1983 | Jobsis et al. | 128/633 |
| 4,510,938 | 4/1985 | Jobsis et al. | 128/633 |
| 4,829,184 | 5/1989 | Nelson et al. | 128/665 |
| 4,913,150 | 4/1990 | Cheung et al. | 128/633 |

FOREIGN PATENT DOCUMENTS

| 0123548 | 10/1984 | European Pat. Off. . |
| 0160768 | 11/1985 | European Pat. Off. . |
| 2054844A | 2/1981 | United Kingdom . |
| 2059053 | 4/1981 | United Kingdom | 128/665 |

OTHER PUBLICATIONS

Yoshiya et al, Med. & Biol. Eng. and Comput., vol. 18, Jan. 1980, p. 27.
Wyatt, J. S. et al., "Quantification of Cerebral Oxygenation and Haemodynamics in Sick Newborn Infants by Near Infrared Spectrophotometry", The Lancet, pp. 1063-1066, Nov. 8, 1986.

*Primary Examiner*—William E. Kamm
*Assistant Examiner*—John Hanley
*Attorney, Agent, or Firm*—Finnegan, Henderson, Farabow, Garrett & Dunner

[57] ABSTRACT

An examination apparatus for measuring the oxygenation in body organs by the near infrared light transmission spectrophotometry. The invention relates to an improvement of an illumination-side fixture and a detection-side fixture. In order to hold optical fibers for introducing infrared light in their natural conditions, the fixtures are equipped with respective prisms for changing light paths by prescribed angles. Also, the fixtures are equipped with respective light-emitting diodes for indicating if the examination apparatus is in its operating condition.

3 Claims, 7 Drawing Sheets

FIG. 4
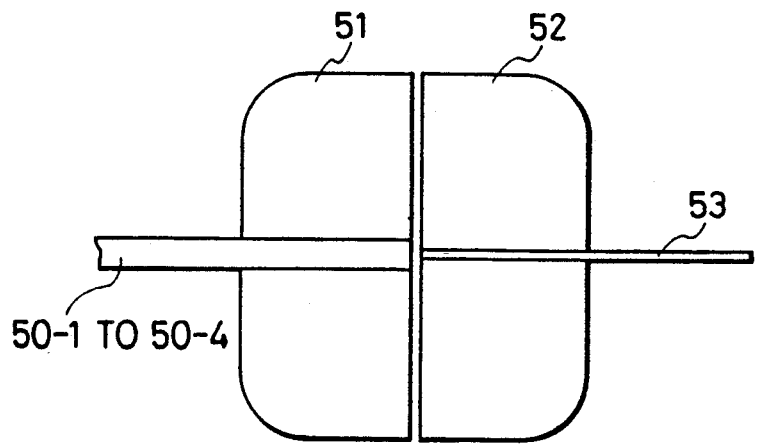
FIG. 5(a)     FIG. 5(b)
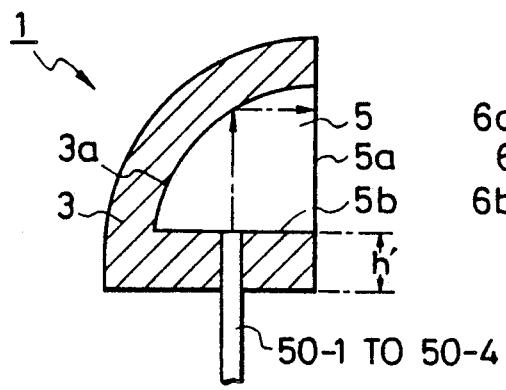 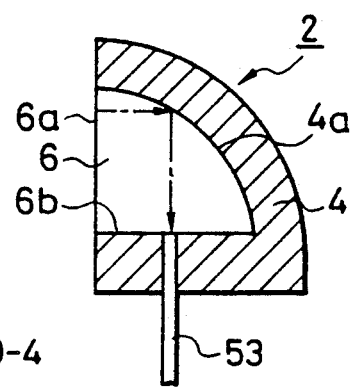
FIG. 7(a)     FIG. 7(b)
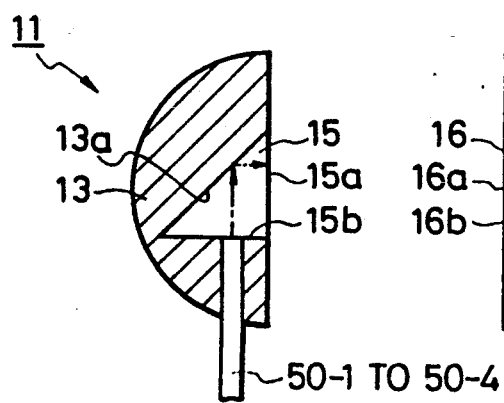 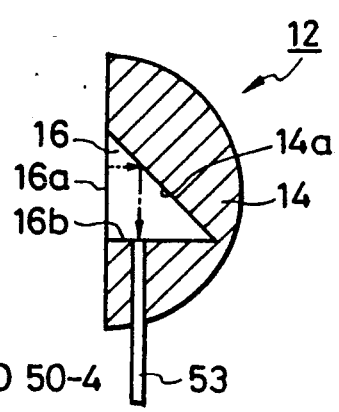

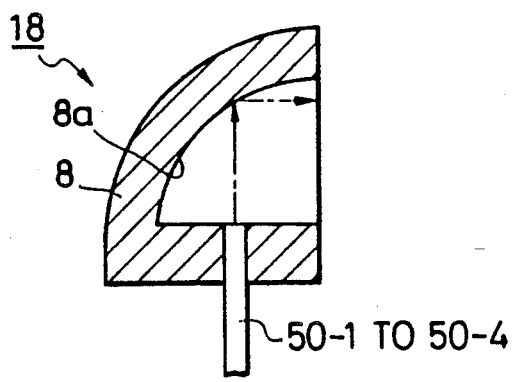
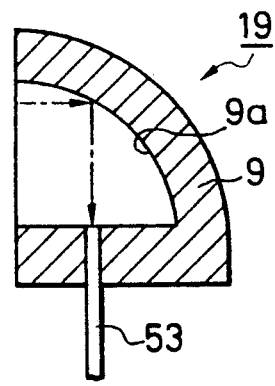
FIG. 8(a)
FIG. 8(b)
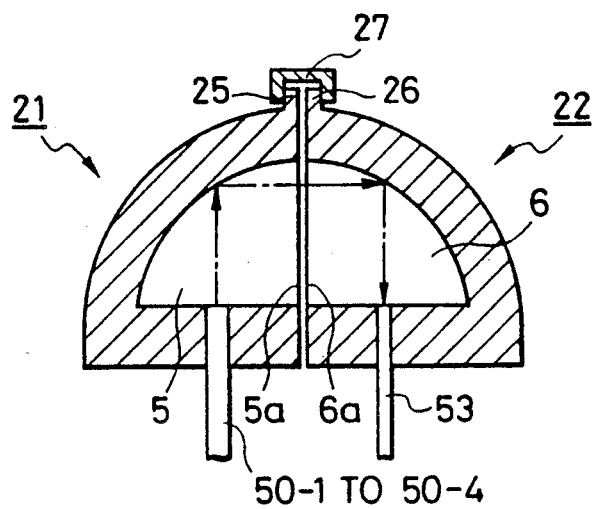
FIG. 9
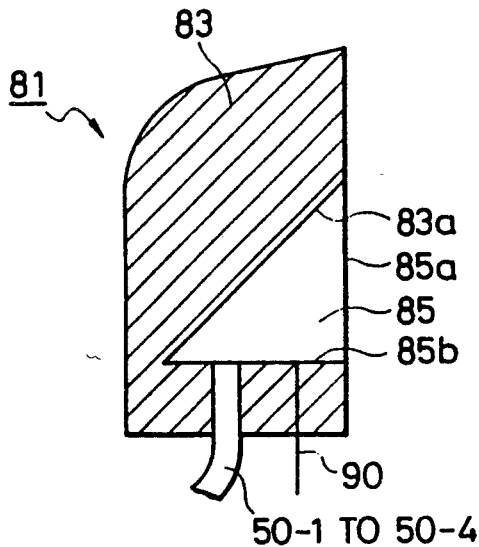
FIG. 10

EXAMINATION APPARATUS FOR MEASURING OXYGENATION IN BODY ORGANS

BACKGROUND OF THE INVENTION

The present invention relates to the apparatus for measuring the oxygen quantity in objects such as the cerebral tissues of a human body or an animal. The invention especially relates to the apparatus for measuring the oxygenation of hemoglobin in blood and of cytochrome in cells by detecting those through electromagnetic waves.

In general, in diagnosing the function of a body organ such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive or that the new-born infant will die is high. Even if the new-born infant lives, however, serious problems in body organs may remain as sequela. The insufficiency of oxygen affects every body organ, but especially causes serious damage in the cerebral tissues.

To examine the oxygen quantity in body organs readily and at the early stage of illness, an examination apparatus disclosed in U.S. Pat. No. 4,281,645 patented on Aug. 4, 1981 has been developed. In this kind of examination apparatus, the variation of oxygen quantity in body organs, especially in the brain, is measured through the absorption spectrum of near infrared light. The absorption is caused by the hemoglobin which is an oxygen-carrying medium in blood and the cytochrome a, $a_3$ which performs oxydation-reduction reaction in cells. As shown in FIG. 1(a), the absorption spectra of near infrared light (700 to 1300 nm), $\alpha_{HbO2}$ and $\alpha_{Hb}$ by oxygenated hemoglobin ($HbO_2$) and disoxygenated hemoglobin (Hb), respectively, are different from each other. And as shown in FIG. 1(b), the absorption spectra of $\alpha_{CyO2}$ and $\alpha_{Cy}$ by oxidized cytochrome a, $a_3$ ($CyO_2$) and reduced cytochrome a, $a_3$ (Cy), respectively, are different from each other. This examination apparatus utilizes the above-described absorption spectra of near infrared light. Four near infrared light rays with different wavelengths, $\lambda_1$, $\lambda_2$, $\lambda_3$ and $\lambda_4$ (e.g. 775 nm, 800 nm, 825 nm and 850 nm) are applied to one side of the patient's head with a time-sharing method and the transmission light rays from the opposite side of the head are in turn detected. By processing these four detected light rays with the prescribed calculation program the density variations of oxygenated hemoglobin ($HbO_2$), disoxygenated hemoglobin (Hb), oxidized cytochrome a, $a_3$ ($CyO_2$) and reduced cytochrome a, $a_3$ (Cy) are calculated. These parameters, in turn, determine the variation of cerebral oxygen quantity.

FIG. 2 shows a system outline of the above-described conventional examination apparatus 45. The conventional examination apparatus 45 includes; light sources such as laser diodes LD1 to LD4 which emit four near infrared light rays with different wavelengths of $\lambda_1$, $\lambda_2$, $\lambda_3$ and $\lambda_4$, respectively; a light source control device 55 which controls output timing of the light sources LD1 to LD4; optical fibers 50-1 to 50-4 which introduces near infrared light rays emitted by the light sources LD1 to LD4 to a patient's head 40; an illumination-side fixture 51 which bundles and holds end portions of the optical fibers 50-1 to 50-4; a detection-side fixture 52 which is fitted to the prescribed position of the opposite side of the patient's head 40; an optical fiber 53 which is held by the detection-side fixture 52 and introduces transmitted near infrared light from the patient's head 40; a transmission light detection device 54 which measures transmission quantity of near infrared light by counting photons of near infrared light introduced by the optical fiber 53; and a computer system 56 which controls the total examination apparatus and determines the variation of oxygen quantity in cerebral tissues being based on the transmission quantity of near infrared light.

The computer system 56 is equipped with a processor 62, a memory 63, output devices 64 such as a display and a printer, and an input device 65 such as a keyboard, and these devices are connected to each other by a system bus 66. The light source control device 55 and the transmission light detection device 54 are connected to the system bus 66 as external I/O's.

The light source control device 55 receives instructions from the computer system 56 and drives the light sources LD1 to LD4 by respective driving signals ACT1 to ACT4 as shown in FIGS. 3(a) to 3(d). As shown in FIG. 3 one measuring period $M_k$ (k=1, 2, ...) consists of N cycles of CY1 to CYn. At a phase $\phi n1$ in an arbitrary cycle CYn, no light source of LD1 to LD4 is driven and therefore the patient's head 40 is not illuminated by the near infrared light from the light sources LD1 to LD4. At the phase $\phi n2$ the light source LD1 is driven and the near infrared light with the wavelength of, for example, 775 nm is emitted from it. In the same manner, at the phase $\phi n3$ the light source LD2 is driven and the near infrared light with the wavelength of, for example, 800 nm is emitted from it; at the phase $\phi n4$ the light source LD3 is driven and the near infrared light with the wavelength of, for example, 825 nm is emitted from it; and at the phase $\phi n5$ the light source LD4 is driven and the near infrared light with the wavelength of, for example, 850 nm is emitted from it. In this manner the light source control device 55 drives the light sources LD1 to LD4 sequentially with a time-sharing method.

Referring again to FIG. 5, the transmission light detection device 54 is equipped with a filter 57 which adjusts the quantity of near infrared light outputted to lenses 70 and 71 from the optical fiber 53; a photomultiplier tube 58 which converts the light from the filter 57 into pulse current and outputs it; an amplifier 59 which amplifies the pulse current from the photomultiplier tube 58; an amplitude discriminator 60 which eliminates the pulse current from the amplifier 59 whose amplitude is smaller than the prescribed threshold value; a multichannel photon-counter 61 which detects photon frequency in every channel; a detection controller 67 which controls detection periods of the multi-channel photon-counter 61; and a temperature controller 68 which controls the temperature of a cooler 69 containing the photomultiplier tube 58.

To use the above-described examination apparatus, the illumination-side fixture and the detection-side fixture are firmly fitted to the prescribed positions of the patient's head 40 by using tape or the like. Once fitted the light sources LD1 to LD4 are driven by the light source control device 55 as shown in FIGS. 3(a) to 3(d), respectively, so that the four near infrared light rays with different wavelengths are emitted from the light sources LD1 to LD4 sequentially with the time-sharing method, and the light rays are introduced by the optical fibers 50-1 to 50-4 to the patient's head 40. As bones and soft tissues in the patient's head 40 are transparent to the near infrared light, the near infrared light is partially absorbed by hemoglobin in blood and cytochrome a, a₃ in cells and outputted to the optical fiber 53. The optical fiber 53 introduces the light to the transmission light detection device 54. At the phase $\phi$n1 no light source of LD1 to LD4 is driven, and therefore the transmission light detection device 54 detects dark light.

The photomultiplier tube 58 in the transmission light detection device 54 is used with a photon-counting device that has high sensitivity and operates at high response speed. The output pulse current from the photomultiplier tube 58 is sent to the amplitude discriminator 60 through the amplifier 59. The amplitude discriminator 60 eliminates the noise component whose amplitude is smaller than the prescribed amplitude threshold and sends only the signal pulse to the multi-channel photon-counter 61. The multi-channel photon-counter 61 detects photons only in the periods $T_o$. The periods $T_o$ are synchronized with the driving signals ACT1 to ACT4 for the respective light sources LD1 to LD4 as shown in FIGS. 3(a) to 3(d) by a control signal CTL as shown in FIG. 3(e). The control signal CTL is generated by the detection controller 67. The multi-channel photon-counter then counts detected photons of every light with each wavelength sent from the optical fiber 53. The transmission data of every near infrared light with each wavelength are obtained through the abovedescribed procedure.

That is, as shown in FIGS. 3(a) to 3(e), at the phase $\phi$n1 in the cycle CYn of light source control device 55 no light source of LD1 to LD4 is driven, therefore the dark light data d are counted by the transmission light detection device 54. At the phases $\phi$n2 to $\phi$n5 the light sources LD1 to LD4 are sequentially driven with the time-sharing method and the transmission light detection device 54 sequentially counts the transmission data $t_{\lambda_1}$, $t_{\lambda_2}$, $t_{\lambda_3}$ and $t_{\lambda_4}$ of the respective near infrared light rays with different wavelengths $\lambda_1$, $\lambda_2$, $\lambda_3$ and $\lambda_4$.

The counting of the dark light data d and the transmission data $t_{\lambda_1}$, $t_{\lambda_2}$, $t_{\lambda_3}$ and $t_{\lambda_4}$ which is sequentially performed in the cycle CYn, is continued N times from CY1 to CYn. That is, one measuring period $M_k$ (k=1, 2, ...) includes N cycles. A concrete example is as follows; if one cycle is 200 $\mu$sec and N is 10000, the measuring period $M_k$ becomes 2 sec. At the time of finishing of One measuring period $M_k$, the counting result of the dark light data $$D\left( = \sum_{n=1}^{N} d/CYn \right)$$

and the counting results of the transmission data $T_{\lambda_1}$, $T_{\lambda_2}$, $T_{\lambda_3}$ and $T_{\lambda_4}$ $$\left( = \sum_{n=1}^{N} t_{\lambda_j}/CYn \right)$$

are transferred to the computer system 56 and stored in the memory 63.

The processor 62 performs the subtraction of the dark light component by using the combination of the transmission data and the dark data $(T_{\lambda_1}, T_{\lambda_2}, T_{\lambda_3}, T_{\lambda_4}, D)M_k$ being stored in the memory 63 after one measuring period $M_k$ and the combination of those $(T_{\lambda_1}, T_{\lambda_2}, T_{\lambda_3}, T_{\lambda_4}, D)M_o$ at the start of measuring, and calculates the variation rates of the transmission light $\Delta T_{\lambda_1}$, $\Delta T_{\lambda_2}$, $\Delta T_{\lambda_3}$ and $\Delta T_{\lambda_4}$. That is, the variation rates of the transmission light $\Delta T_{\lambda_1}$, $\Delta T_{\lambda_2}$, $\Delta T_{\lambda_3}$ and $\Delta T_{\lambda_4}$ are calculated as:

$$\Delta T_{\lambda j} = \log[(T_{\lambda j} - D)_{mk}/(T_{\lambda j} - D)_{Mo}] (j = 1 \text{ to } 4). \quad (1)$$

The use of logarithm in the above calculation of $\Delta T_{\lambda j}$ is to express the variation as an optical density.

Using the above-calculated variation rates of the transmission light $\Delta T_{\lambda_1}$, $\Delta T_{\lambda_2}$, $\Delta T_{\lambda_3}$ and $\Delta T_{\lambda_4}$, density variations of oxygenated hemoglobin (HbO₂), disoxygenated hemoglobin (Hb), oxidized cytochrome a, a₃ (CyO₂) and reduced cytochrome a, a₃ which are expressed as $\Delta X_{HbO2}$ $\Delta X_{ab}$, $\Delta X_{CyO2}$ and $\Delta X_{cy}$, respectively, can be determined. That is, each of density variations of $\Delta X_{HbO2}$ $\Delta X_{Hb}$, $\Delta X_{CyO2}$ and $\Delta X_{cy}$ is calculated as:

$$\Delta X_i = \sum_{j=1}^{4} (a_{ij})^{-1} \Delta T_{\lambda j}/l \quad (2)$$

where $\Delta_{ij}$ is an absorption coefficient of each component i (HbO₂, Hb, CyO₂, Cy) for each wavelength $\lambda_j$ ($\lambda_1$, $\lambda_2$, $\lambda_3$, $\lambda_4$) and is predetermined from FIGS. 1(a) and 1(b), and l is the length of the patient's head 40 along the travelling direction of the near infrared light.

As the above-detected density variation components, $\Delta X_{Hbo2}$, $\Delta X_{Hb}$, $\Delta X_{CyO2}$ and $\Delta X_{Cy}$, reflect the variation of oxygen quantity in the brain, the variation of oxygen quantity in the brain can be determined by outputting these detected results from the output device 64. The diagnosis is thus made based on these results.

The illumination-side fixture 51 and the detection-side fixture 52 of the foregoing examination apparatus hold the optical fibers 50-1 to 50-4 and the optical fiber 53, respectively, in such a manner that the fibers are perpendicular to the outer skin layer of the head 40 as shown in FIG. 2, in order to make the near infrared light perpendicularly incident on the head 40 and also make the transmission light perpendicularly incident on the optical fiber 53 so as to obtain maximum illumination efficiency and detection efficiency.

However, when the illumination-side fixture 51 and the detection-side fixture 52 are fitted to the head 40 in the actual use, the optical fibers (glass fibers) 50-1 to 50-4 and 53 which can just be bent to a comparatively large radius of curvature are required to be bent by prescribed degrees as shown in FIG. 2. And it is not easy to make these fixtures 51 and 52 firmly fit to the head 40. If the head 40 is moved in the midst of the measurement, the fitting positions of these fixtures are likely to be changed, resulting in a difficulty in performing an accurate measurement. Also with the structure of these fixtures, there exist limits in shortening the lengths of the optical fibers 50-1 to 50-4 and 53 in order to reduce transmission losses in the fibers of the near infrared light rays emitted from the light sources LD1 to LD4 or transmitted from the head 40.

It is necessary that the illumination-side fixture 51 and the detection-side fixture 52 hold the optical fibers 50-1 to 50-4 and the optical fiber 53 by prescribed lengths respectively, in order to always keep the optical fibers 50-1 to 50-4 and 53 perpendicular to the outer skin layer of the head 40. Therefore, the fixtures 51 and 52 become so large that they cannot be fitted easily to the head 40 by a tape for intercepting ambient light.

It is desired that the fixtures 51 and 52 can be assembled together opposite to each other as shown in FIG. 4 when they are stored, in the custody of, or used, in order to prevent that the contact surfaces to the object of the fixtures are damaged or stained when the examination apparatus is not in use, or in order to inspect the examination apparatus itself. But, the conventional fixtures 51 and 52 are not suitable for being assembled together opposite each other when they are stored, in the custody of, or used, because they hold the respective optical fibers 50-1 to 50-4 and 53 so that the optical fibers are perpendicular to the outer skin layer of the head 40.

On the other hand, the conventional examination apparatus 45 has another kind of problems in connection with the fixtures 51 and 52 as described in the following.

When the operator of the examination apparatus fits the illumination-side fixture 51 and the detection-side fixture 52 to the head 40 etc. of the object person or removes those from the head etc., he should confirm that the light sources LD1 to LD4 are not being driven and the photomultiplier tube 58 is not in the operating condition. The light sources LD1 to LD4 should not be driven in fitting or removing the fixtures to prevent the near infrared light rays from being emitted from the illumination-side fixture 51 to the outside. Also, the photomultiplier tube 58 should not be in the operating condition in that situation, because the photomultiplier tube is damaged when the detection-side fixture 52 is faced to an outside bright area.

However, the conventional examination apparatus has the problem that the operator fails to make the above-described confirmation or at least it is not easy for the operator to make the confirmation. This problem is originated from the fact that the illumination-side fixture 51 and the detection-side fixture 52 are connected to the end portions of the respective optical fibers 50-1 to 50-4 and 53, the end portions being far from the main body of the examination apparatus.

Another problem in the conventional apparatus is that as in general the fixtures 51 and 52 are comparatively small and have the same shape and color, it is confusing which is the illumination-side fixture or detection-side fixture.

SUMMARY OF THE INVENTION

An object of the present invention is to eliminate the above-described problems accompanying the conventional examination apparatus by improving an illumination-side fixture and a detection-side fixture of an examination apparatus.

More specifically, an object of the invention is to provide an examination apparatus with an illumination-side fixture and a detection-side fixture which can hold optical fibers with their natural conditions.

Another object of the invention is to provide an examination apparatus with the fixtures which can be assembled together and are suitable for storing or inspection of an examination apparatus.

Another object of the invention is to provide an examination apparatus with the fixtures which can indicate if an examination apparatus is in its operating condition.

An examination apparatus according to the first aspect of the invention comprises: an illumination-side fixture for making electromagnetic waves introduced by optical fibers of illumination side incident on a measuring object; and a detection-side fixture for providing electromagnetic waves transmitted from the measuring object to an optical fiber of detection side; wherein the fixtures are equipped with respective optical members therein to change transmission path of the electromagnetic wave by predetermined angles. By utilizing these optical members, the optical fibers of the illumination-side and the detection-side can be naturally held by the respective fixtures without stresses.

An examination apparatus according to the second aspect of the invention comprises: light source means for sequentially emitting electromagnetic waves with different wavelengths; an illumination-side fixture for making the electromagnetic waves from the light source means incident on a measuring object; and a detection-side fixture for providing electromagnetic waves transmitted from the measuring object to a transmission light detection means through an optical fiber; wherein the illumination-side fixture is equipped with first indication means indicating if the electromagnetic waves are being emitted from the light source means and the detection-side fixture is equipped with second indication means indicating if the transmission light detection means is in its operating condition, and the fixtures have different shapes and/or different colors from each other. Accordingly, an operator of the examination apparatus can easily confirm that the electromagnetic waves are not being emitted from the light source means and that the transmission light detection means is not in its operating condition, when he fits or removes the fixtures. Also, the operator can easily avoid such a mistake that the fixtures are fitted to the object with being replaced with each other.

Other and further objects, features and advantages of the invention will appear more fully from the following description taken in connection with the accompanying drawings.

BRIEF DESCRIPTION OF THE DRAWINGS

FIG. 4 is a sectional view showing an assembly of an illumination-side fixture and a detection-side fixture of a conventional examination apparatus;

FIGS. 5(a) and 5(b) are sectional views showing an illumination-side fixture and a detection-side fixture, respectively, according to an embodiment of the invention;

FIGS. 7(a) and 7(b) are sectional views showing an illumination-side fixture and a detection-side fixture, respectively, according to another embodiment of the invention;

FIGS. 8(a) and 8(b) are sectional views showing an illumination-side fixture and a detection-side fixture, respectively, according to another embodiment of the invention;

FIG. 9 is a sectional view showing an assembly of fixtures of FIGS. 5(a) and 5(b);

FIG. 10 is a sectional view showing an illumination-side fixture according to another embodiment of the invention.

DETAILED DESCRIPTION OF THE PREFERRED EMBODIMENTS

Figure 1A:
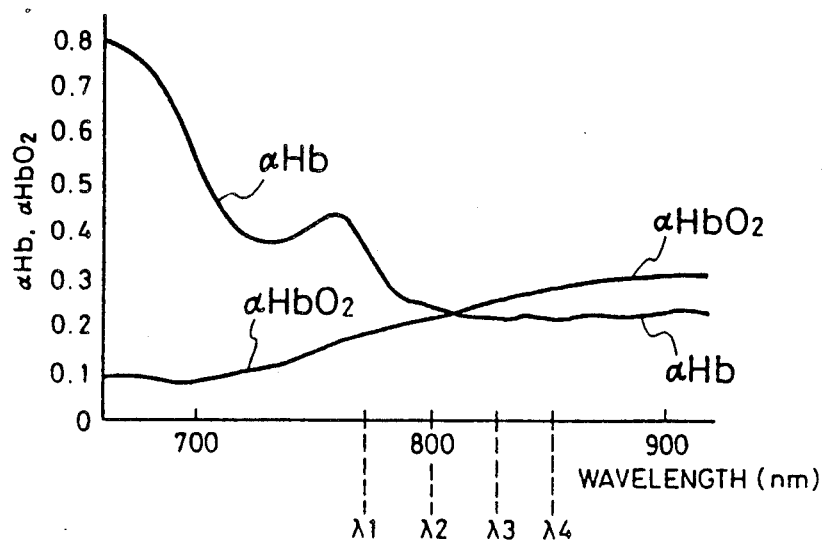
FIGS. 1(a) and 1(b) are graphs showing absorption spectra of hemoglobin and cytochrome, respectively.
Figure 1B:
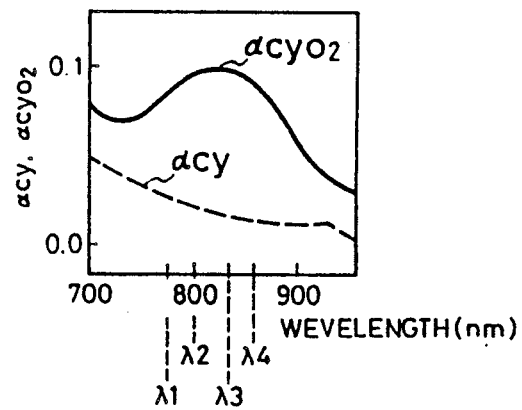

An examination apparatus according to the first aspect of the present invention will be described in the following.

FIGS. 5(a) and 5(b) are sectional views showing an illumination-side fixture and a detection-side fixture, respectively, according to an embodiment of the invention. The illumination-side fixture 1 and the detection-side fixture 2 are equipped with respective prisms 5 and 6 inside. Each of prisms 5 and 6 has a cross section of approximately ¼ of a circle. The prisms 5 and 6 are fitted to inside surfaces 3a and 4a of main bodies 3 and 4, respectively. A surface of light-emitting side 5a of the prism 5 and a surface of light receiving side 6a of the prism 6 are applied to outer skin layers of for example a head of an object person. Optical fibers 50-1 to 50-4 are perpendicularly connected to another surface 5b of the prism 5. An optical fiber 53 is perpendicularly connected to another surface 6b of the prism 6.

Figure 6:
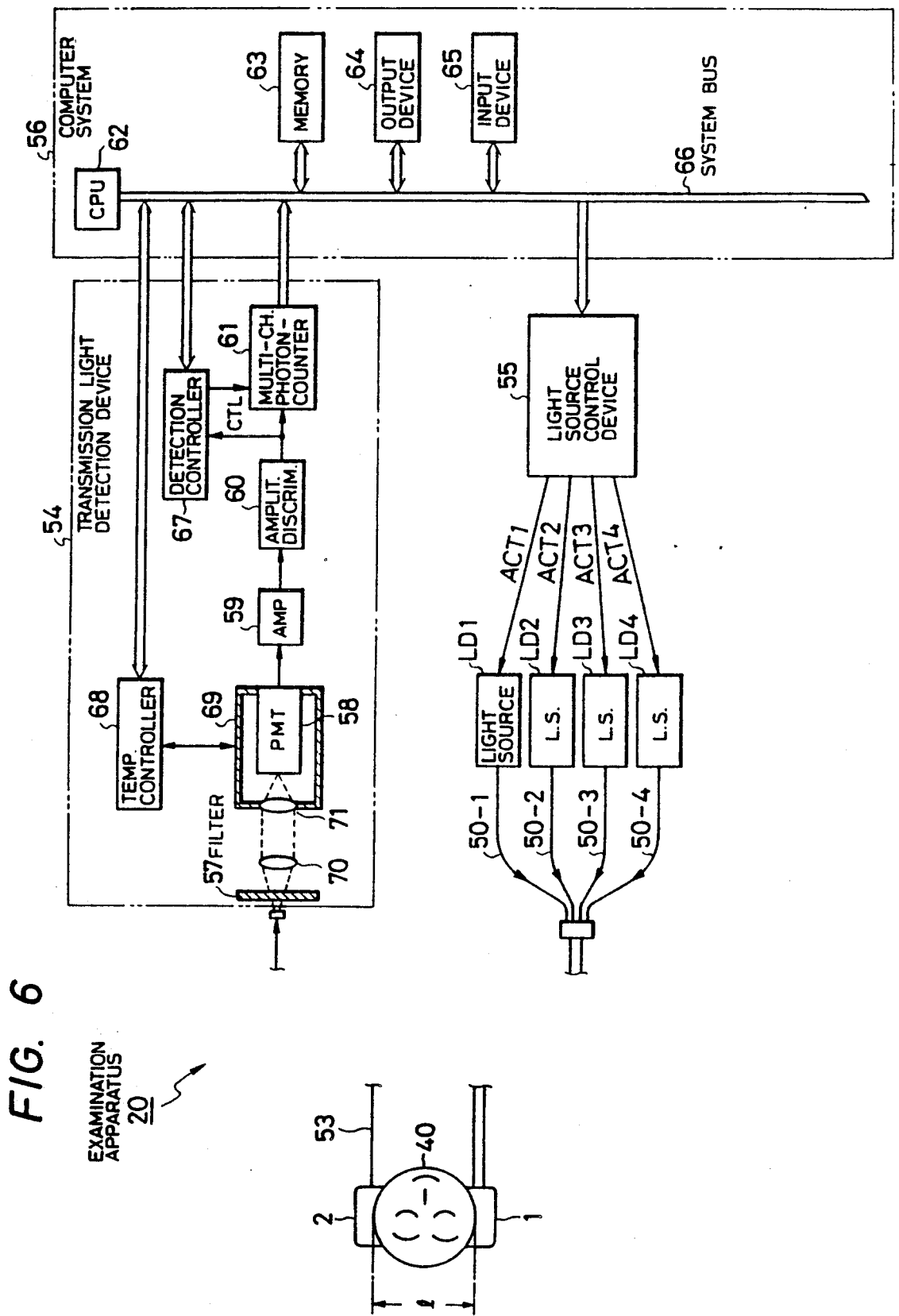
FIG. 6 is a block diagram showing an examination apparatus employing fixtures of FIGS. 5(a) and 5(b)

As shown in FIG. 6, when for example the oxygenation in cerebral tissues in a head 40 of an object person is measured by an examination apparatus 20 equipped with the illumination-side fixture 1 and the detection-side fixture 2, the light-emitting surface 5a of the prism 5 in the illumination-side fixture 1 is applied to the prescribed position of the head 40 and the light-receiving surface 6a of the prism 6 in the detection-side fixture 2 is applied to the prescribed position of an opposite side of the head 40. The optical fibers 50-1 to 50-4 and the optical fiber 53 are extended almost straight from optical fibers LD1 to LD4 and a transmission light detection device 54, respectively, so that these optical fibers are in their natural conditions without receiving stresses. Therefore, since it is not necessary that the optical fibers 50-1 to 50-4 and 53 are bent to a great extent when the illumination-side fixture 1 and the detection-side fixture 2 are fitted to the head 40, the fixtures 1 and 2 can be firmly fitted to the head 40 so that the fitting positions of the fixtures 1 and 2 do not change even if the head 40 is moved. Moreover, as the optical fibers 50-1 to 50-4 are extended from the light sources LD1 to LD4 and from the transmission light detection device 54 in their natural conditions, lengths of these optical fibers can be shortened, thereby reducing transmission losses of near infrared light.

Compared with the conventional illumination-side fixture 51 and detection-side fixture 52, the length h' of the supporting portion of the optical fibers 50-1 to 50-4 and 53 can be shortened and thereby the whole size of the fixtures can also be made smaller, because it is not necessary for the optical fibers 50-1 to 50-4 and 53 to be held much firmly by the fixtures.

When the light sources are driven with the illumination-side fixture 1 and the detection-side fixture 2 shown in FIGS. 5(a) and 5(b), respectively, being fitted to the head, etc., the near infrared light rays emitted from the light sources LD1 to LD4 are perpendicularly made incident on the surface 5b of the prism 5 in the illumination-side fixture 1, reflected by the inner surface 3a of the main body 3 of the illumination-side fixture 1, perpendicularly outputted from the light-emitting surface 5a of the prism 5, and made incident on the head, etc. The near infrared light rays transmitted from the head, etc. are perpendicularly made incident on the light-receiving surface 6a of the prism 6 in the detection-side fixture 2, reflected by the inner surface 4a of the main body 4 of the detection-side fixture 2, and finally outputted from the surface 6b perpendicularly to the optical fiber 53. An accurate measurement can be performed with these structures of the fixtures.

FIGS. 7(a) and 7(b) show another embodiment of the illumination-side fixture and the detection-side fixture, respectively. An illumination-side fixture 11 and a detection-side fixture 12 are equipped with right-angled prisms 15 and 16, respectively, inside. The right-angled prisms 15 and 16 are fitted to inside surfaces 13a and 14a of the main bodies 13 and 14, respectively. As in the same manner as the illumination-side fixture 1 and the detection-side fixture 2 shown in FIGS. 5(a) and 5(b), the light-illuminating surface 15a and the light-receiving surface 16a of the right-angled prisms 15 and 16 are applied to the head, etc. of an object person and the optical fibers 50 1 to 50-4 and 53 are perpendicularly connected to the surfaces 15b and 16b of the right-angled prisms 15 and 16, respectively.

FIGS. 8(a) and 8(b) show another embodiment of the illumination-side fixture and the detection-side fixture, respectively. Inner surfaces 8a and 9a of main bodies 8 and 9 of an illumination-side fixture 18 and a detection-side fixture 19, respectively, have received treatment of light reflection. A shape of cross section of the inner surface of the fixture main body may be approximately ¼ of a circle as shown in FIGS. 8(a) and 8(b), or a straight line.

The illumination-side fixtures 11 and 18 and the detection-side fixtures 12 and 19 with above-described structures have the same advantages as the illumination-side fixture 1 and the detection-side fixture 2, that is, these fixtures can be applied to the head, etc. easily and firmly and the sizes of these fixtures can be made smaller.

FIG. 9 is a sectional view of an illumination-side fixture and a detection-side fixture with structures suitable for being stored, in the custody of or an inspection of the examination apparatus itself.

An illumination-side fixture 21 and a detection-side fixture 22 in FIG. 9 have flanges 25 and 26, respectively, at the peripheries of the contact sides to the other fixture and the flanges 25 and 26 are fitted into a clasper 27.

When the examination apparatus is not in use, by fitting the illumination-side fixture 21 and the detection-side fixture 22 to each other in close contact by the aid of the clasper 27, the light-illumination surface 5a and the light-receiving surface 6a of the prisms 5 and 6 can be effectively prevented from being damaged or stained.

When the examination apparatus itself is inspected, the optical system in the examination apparatus can be inspected by making the near infrared light irradiated from the illumination-side fixture 21 directly incident on the detection side fixture 22.

In the above both situations, as the optical fibers 50-1 to 50-4 and 53 are kept in their natural conditions, the optical fibers 50-1 to 50-4 and 53 can be prevented from being broken or plastically deformed by bending. The optical fibers 50-1 to 50-4 and 53 can be kept in their natural conditions when the fixtures 21 and 22 are stored, had the custody of, or in use.

Though the clasper 27 is used in the embodiment in FIG. 9, the clasper can be eliminated by making the illumination-side fixture 21 and the detection-side fixture 22 include means for fitting themselves to each other.

FIG. 10 is a sectional view showing another embodiment of the illumination-side fixture which is used to watch the change of fitting position of the illumination-side fixture by utilizing a reflected light from for example the head of the object person. The illumination-side fixture 81 has a prism 85. The prism 85 is a right-angled prism and fitted to an inside surface 83a of a main body 83 which has received a treatment of light reflection. One surface 85a of the prism 85 is applied to the head and the emitted near infrared light rays are introduced by the optical fibers 50-1 to 50-4 to the other surface 85b. The light rays are reflected by the inner surface 83a and incident on the head. The reflected light from the head is received by the end of the optical fiber 90 on the surface 85b. Obviously, the prism with a cross section of approximately ¼ of a circle can also be employed. Moreover, the detection-side fixture may also employ the similar structure to that in FIG. 10 to watch the change of fitting position of the detection-side fixture. The same advantages as with the foregoing embodiments can be obtained with the structure shown in FIG. 10.

Though in the foregoing embodiments the prisms 5 and 6 with the cross section of approximately ¼ of a circle or the right-angled prisms 15, 16 and 85 are employed, other prisms with a known shape may be used. The angle of light-path change by the prism or the inner surface of the fixture main body is not limited to 90 degrees, but other optical member which changes the light-path by a prescribed angle may be used. And in this case, the optical fibers 50-1 to 50-4 and 53 may not be held perpendicularly to the prescribed surfaces of the optical members.

Another aspect of the present invention will be described in the following on the basis of the drawing.

Figure 2:
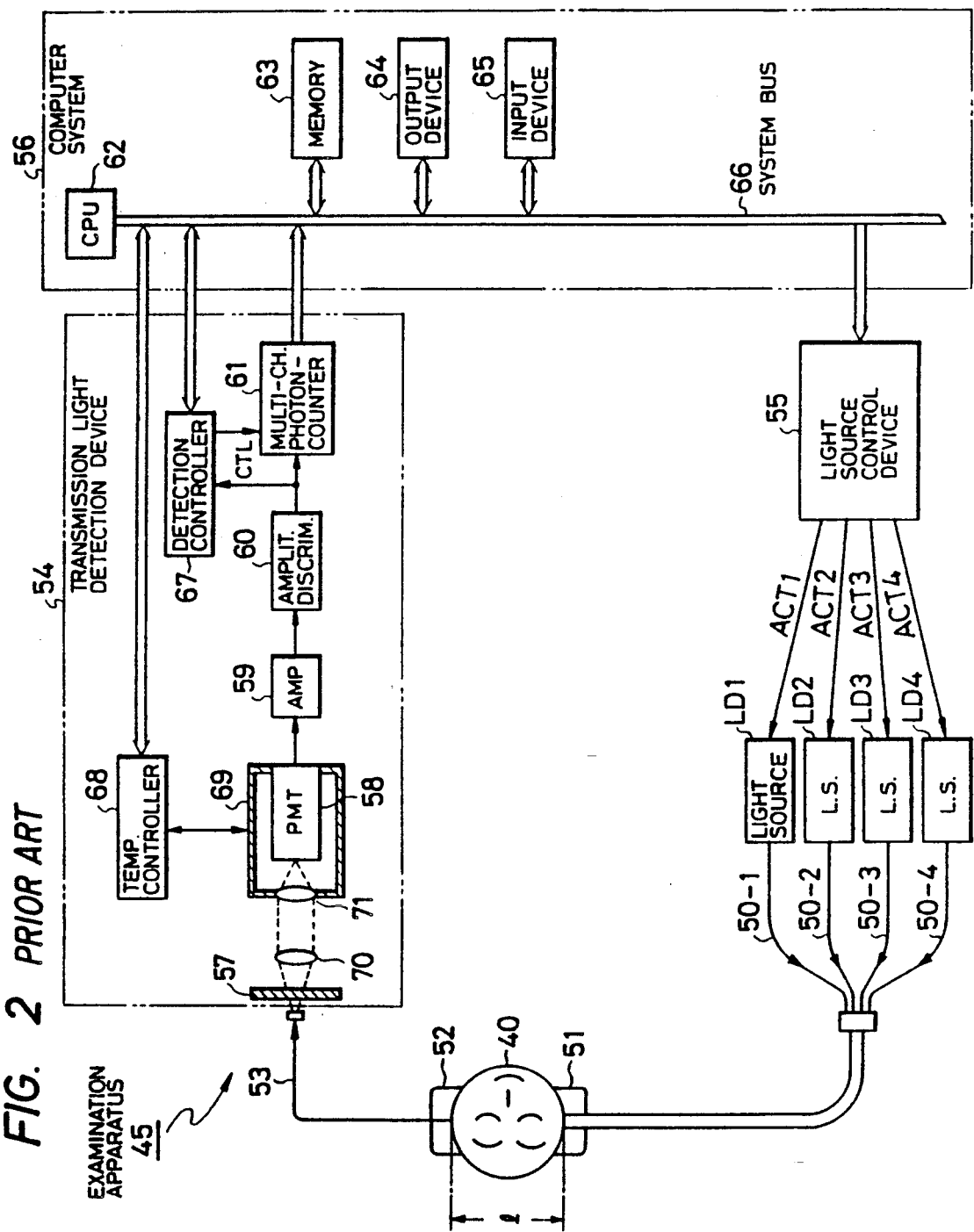
FIG. 2 is a block diagram showing a system constitution of a conventional examination apparatus.
Figure 3:
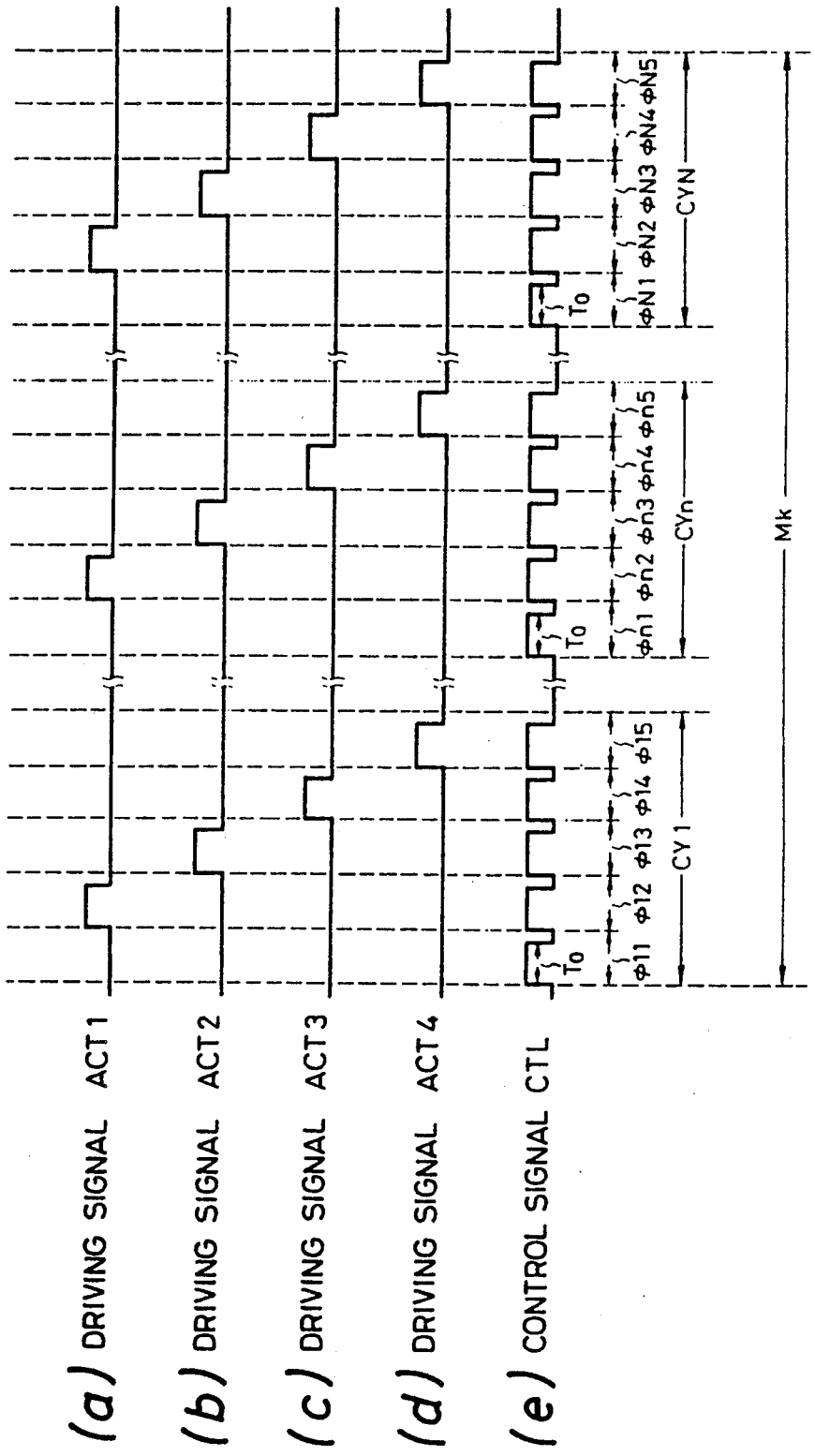
FIGS. 3(a) to 3(e) are time-charts of driving signals ACT1 to ACT4 and a control signal CTL, respectively.
Figure 11:
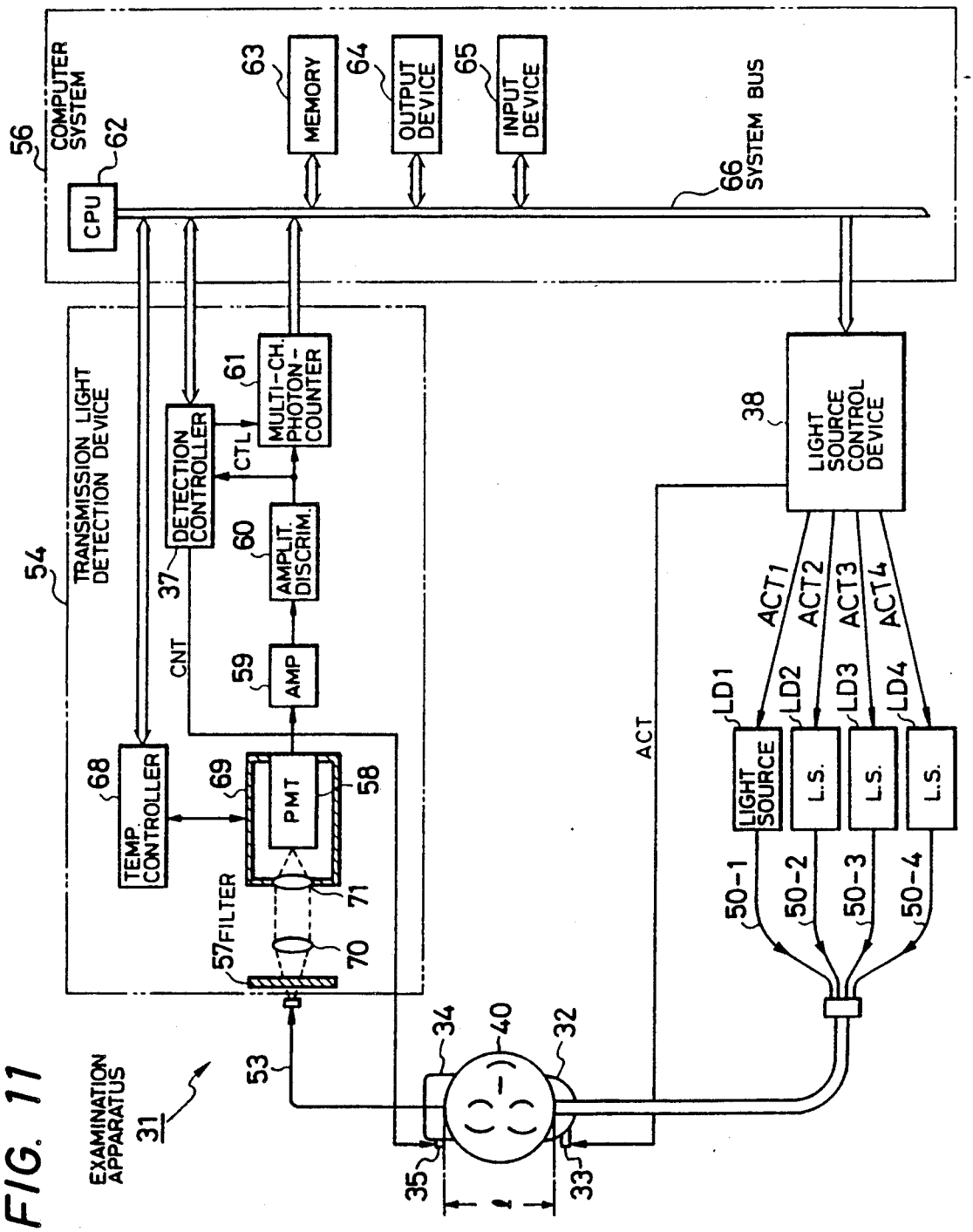
FIG. 11 is a block diagram showing an examination apparatus employing an illumination-side fixture and a detection-side fixture according to another embodiment of the invention.

FIG. 11 shows a system constitution of an examination apparatus according t another embodiment of the invention. In FIG. 11, the same blocks, parts and signals as in FIG. 2 are designated by the same reference numerals or characters as those in FIG. 2 and the explanation for these blocks, parts and signals will be eliminated.

In an examination apparatus 31, an illumination-side fixture 32 and a detection side fixture 34 are equipped with light-emitting diodes 33 and 35 respectively. The light-emitting diode 33 equipped in the illumination-side fixture 32 is connected to a light source control device 38 and the light-emitting diode 35 equipped in the detection-side fixture 34 is connected to a detection controller 37. While the light source control device 38 drives light sources LD1 to LD4 through respective driving signals ACT1 to ACT4 as shown in FIGS. 3(a) to 3(d) as in the same manner as the conventional light source control device 55, it makes the light-emitting diode 33 emit light by providing the light emitting diode 33 with a driving signal ACT when the driving signals ACT1 to ACT4 are outputted from the light source control device 38.

The detection controller 37 senses if a photomultiplier tube 58 is in its operating condition through the computer system 56 and makes light-emitting diode 35 emit light by providing a signal CNT according to information sent from the computer system 56.

Furthermore, shapes and/or colors of the illumination-side fixture 32 and detection-side fixture 34 are different from each other. Instead of making the shapes and/or colors of the fixtures 32 and 34 different from each other, colors of emitted light from the light-emitting diodes 33 and 35 may be made different from each other. Or, both of the shapes and/or colors of the fixtures and the colors of emitted light from the light-emitting diodes may be made different from each other.

For example, while the shape and color of the illumination-side fixture 32 are made a half sphere and red, respectively, those of the detection-side fixture 34 are made a rectangular parallelepiped and blue, respectively. While the color of the emitted light from the light-emitting diode 33 is made red, that from the light-emitting diode 35 is made blue.

When the illumination-side fixture 32 and the detection-side fixture 34 of the examination apparatus 31 are applied to the head 40, etc. of the object person, an operator checks whether the light-emitting diode 33 of the illumination-side fixture 32 and the light-emitting diode 35 of the detection-side fixture 34 are emitting light or not. If both of diodes 33 and 35 are emitting light, the operator can immediately know that the light sources LD1 to LD4 are being driven and the near infrared light rays are being emitted from the illumination-side fixture 32 and also the photomultiplier tube 58 is in its operating condition. If only one of the diodes 33 and 35 is emitting light, the operator immediately known that the light sources LD1 to LD4 are being driven or the photomultiplier tube 58 is in its operating condition, on the basis of the color of the emitted light from the light-emitting diode or the shape and color of the fixture whose light-emitting diode is emitting light.

As the operator can discriminate the fixtures according to the shape and color of the fixtures, a mistake of applying the wrong fixture to the head 40, etc. can be avoided.

The operator can know if the examination apparatus 31 is normally operating by checking if the light-emitting diodes 33 and 35 are emitting light, because the light-emitting diodes 33 and 35 should be emitting light when an actual examination is being performed with the illumination-side fixture 32 and the detection-side fixture 34 being applied to the head 40, etc. of the object person.

Though in the foregoing embodiments the plural light sources are employed, the plural electromagnetic waves with different wavelengths may be obtained by using only one white light source and filtering emitted white light. The application of the examination apparatus of the invention is not limited to the medical field, but covers many fields including mere measurements. The measuring objects are not limited to the body organs, but may be general objects such as a piece of flesh. The electromagnetic wave emitted from the light source is not limited to the near infrared light, but may be far infrared light, visible light or a microwave.

What is claimed is:

1. An examination apparatus for measuring the oxygenation in an object with electromagnetic wave transmission spectrophotometry, comprising:
   light source means for sequentially emitting electromagnetic waves with respective different wavelengths;

illumination-side fixture means for guiding the electromagnetic waves introduced from the light source means onto a measuring object;

detection-side fixture means for detecting electromagnetic waves transmitted from the measuring object and sending the transmitted electromagnetic waves to transmission light detection means;

transmission light detection means for detecting the transmitted electromagnetic waves introduced from the detection-side fixture means and outputting transmission light data to a computer system means; and computer system means for controlling the light source means and the transmission light detection means and calculating the oxygenation in the measuring object; wherein the illumination-side fixture means is equipped with a first indication means for indicating if the electromagnetic waves are being emitted from the light source means; and the detection-side fixture means is equipped with a second indication means for indicating if the transmission light detection means is in its operating condition; and shapes and/or colors of the illumination-side fixture means and the detection-side fixture means are different from each other.

2. An examination apparatus as claimed in claim 1, wherein the first and second indication means are a first light-emitting diode and a second light-emitting diode, respectively.

3. An examination apparatus as claimed in claim 2, wherein colors of light rays emitted from the first and second light-emitting diodes are different from each other.

* * * * *